United States Patent

Itai

(10) Patent No.: US 10,398,286 B2
(45) Date of Patent: Sep. 3, 2019

(54) MEDICAL IMAGE DISPLAY CONTROL APPARATUS, METHOD, AND PROGRAM

(71) Applicant: FUJIFILM Corporation, Tokyo (JP)

(72) Inventor: Yoshinori Itai, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 637 days.

(21) Appl. No.: 14/855,602

(22) Filed: Sep. 16, 2015

(65) Prior Publication Data

US 2016/0000299 A1 Jan. 7, 2016

Related U.S. Application Data

(63) Continuation of application No. PCT/JP2014/000357, filed on Jan. 24, 2014.

(30) Foreign Application Priority Data

Mar. 22, 2013 (JP) .................................. 2013-059673

(51) Int. Cl.
*A61B 1/00* (2006.01)
*A61B 6/00* (2006.01)
(Continued)

(52) U.S. Cl.
CPC ........ *A61B 1/00006* (2013.01); *A61B 1/0005* (2013.01); *A61B 1/00009* (2013.01);
(Continued)

(58) Field of Classification Search
CPC ............ A61B 1/00006; A61B 1/00009; A61B 1/00045; A61B 1/0005; A61B 1/31
(Continued)

(56) References Cited

U.S. PATENT DOCUMENTS 6,456,735 B1 * 9/2002 Sato ...................... G06T 19/003
382/131
7,194,117 B2 * 3/2007 Kaufman ............... A61B 5/055
378/41
(Continued)

FOREIGN PATENT DOCUMENTS

EP   1 983 487 A2   10/2008
JP   11-076228 A   3/1999
(Continued)

OTHER PUBLICATIONS

Communication dated May 6, 2016, from the Japanese Patent Office in corresponding application No. 2013-059673.
(Continued)

*Primary Examiner* — Timothy J Neal
*Assistant Examiner* — Jae Woo
(74) *Attorney, Agent, or Firm* — Sughrue Mion, PLLC

(57) ABSTRACT

Providing an inner wall image generation unit that generates, based on a three-dimensional image of a subject, an inner wall image representing the inner wall of a hollow organ of the subject, a specific region projection image generation unit that obtains a representative value based on a plurality of voxels on a light ray vector extending outside the hollow organ by a preset distance from each pixel of the inner wall image and generates a specific region projection image by projecting the representative value on the inner wall image, and a display control unit that superimposingly displays the specific region projection image on the inner wall image, wherein the specific region projection image generation unit sets some visualization target voxels from the voxels of the three-dimensional image, and obtains a representative value of a visualization target voxel in the plurality of voxels on the light ray vector.

11 Claims, 4 Drawing Sheets

(51) Int. Cl.
*A61B 1/31* (2006.01)
*A61B 1/313* (2006.01)

(52) U.S. Cl.
CPC ............ *A61B 1/00045* (2013.01); *A61B 1/31* (2013.01); *A61B 1/3137* (2013.01); *A61B 6/5223* (2013.01)

(58) Field of Classification Search
USPC .................. 600/111, 117, 118, 166, 173
See application file for complete search history.

(56) References Cited

U.S. PATENT DOCUMENTS

| | | | | |
|---|---|---|---|---|
| 7,486,811 | B2 * | 2/2009 | Kaufman | G06T 7/0012 378/21 |
| 7,778,451 | B2 * | 8/2010 | Matsumoto | G06T 15/08 345/420 |
| 7,825,924 | B2 * | 11/2010 | Matsumoto | G06T 19/00 345/419 |
| 8,611,988 | B2 * | 12/2013 | Miyamoto | A61B 6/032 600/424 |
| 2005/0281481 | A1 * | 12/2005 | Guendel | A61B 6/466 382/276 |
| 2006/0103670 | A1 * | 5/2006 | Matsumoto | G06T 15/08 345/626 |
| 2006/0279568 | A1 * | 12/2006 | Matsumoto | G06T 19/00 345/419 |
| 2007/0154075 | A1 * | 7/2007 | Matsumoto | A61B 6/463 382/128 |
| 2010/0142788 | A1 * | 6/2010 | Matsumoto | G06T 11/008 382/131 |
| 2010/0265251 | A1 * | 10/2010 | Vining | G06T 7/11 345/420 |
| 2011/0026795 | A1 * | 2/2011 | Leber | A61B 6/037 382/131 |
| 2011/0166418 | A1 | 7/2011 | Aoyagi et al. | |
| 2011/0299746 | A1 | 12/2011 | Kobayashi et al. | |
| 2012/0026162 | A1 | 2/2012 | Masumoto | |
| 2012/0033866 | A1 * | 2/2012 | Masumoto | A61B 5/4255 382/128 |
| 2012/0136208 | A1 * | 5/2012 | Itai | G06T 19/003 600/109 |
| 2012/0230559 | A1 | 9/2012 | Itai | |
| 2013/0137926 | A1 * | 5/2013 | Itai | A61B 1/0005 600/111 |
| 2015/0002547 | A1 * | 1/2015 | Itai | A61B 6/463 345/634 |
| 2015/0085092 | A1 * | 3/2015 | Takemura | A61B 1/00009 348/65 |
| 2015/0178989 | A1 * | 6/2015 | Itai | A61B 6/03 382/131 |

FOREIGN PATENT DOCUMENTS

| | | |
|---|---|---|
| JP | 2000-048168 A | 2/2000 |
| JP | 2005-349199 A | 12/2005 |
| JP | 2007-181532 A | 7/2007 |
| JP | 2008-054763 A | 3/2008 |
| JP | 2008-259712 A | 10/2008 |
| JP | 2008-259713 A | 10/2008 |
| JP | 2010-264232 A | 11/2010 |
| JP | 2011-139797 A | 7/2011 |
| JP | 2012-016575 A | 1/2012 |
| JP | 2012-024517 A | 2/2012 |
| JP | 2012-187161 A | 10/2012 |
| JP | 2013-000431 A | 1/2013 |
| WO | 2009/107770 A1 | 9/2009 |

OTHER PUBLICATIONS

Reza A. Zoroofi, et al., "Segmentation of Pelvis and Femur from Computer Tomography Images", IEICE Technical Report, MI, Medical Image, Jan. 2001, pp. 99-104, vol. 100, No. 596.
International Search Report for PCT/JP2014/000357 dated Jun. 3, 2014 [PCT/ISA/210].
Written Opinion for PCT/JP2014/000357 dated Jun. 3, 2014 [PCT/ISA/237].

* cited by examiner

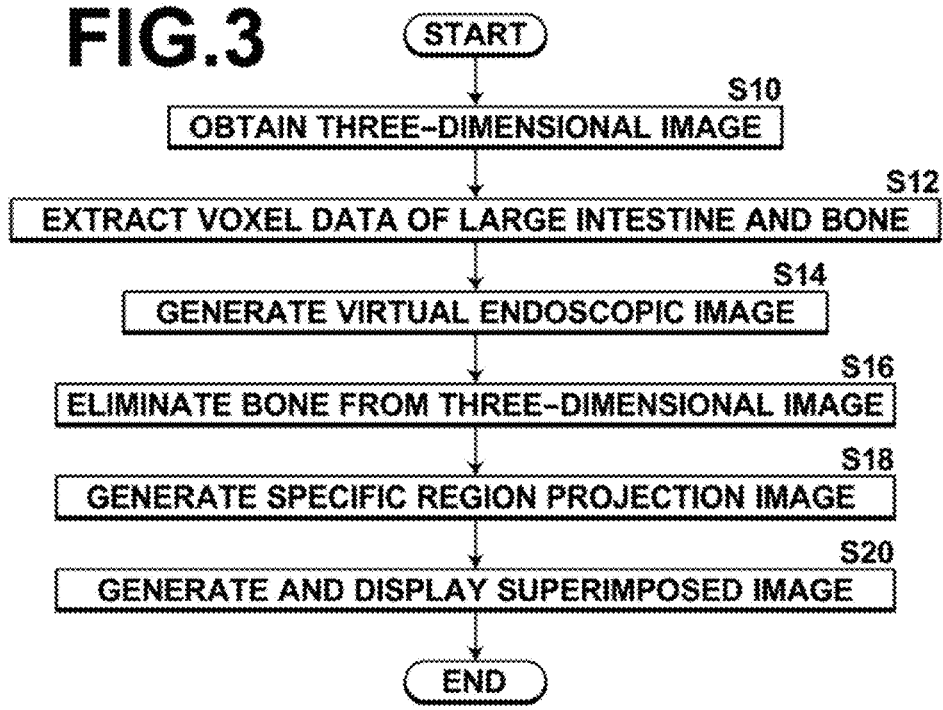
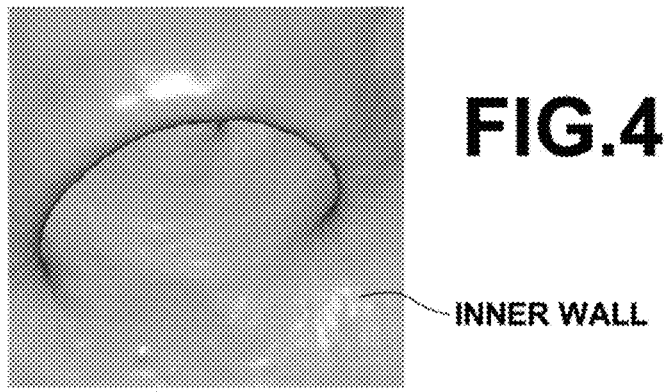
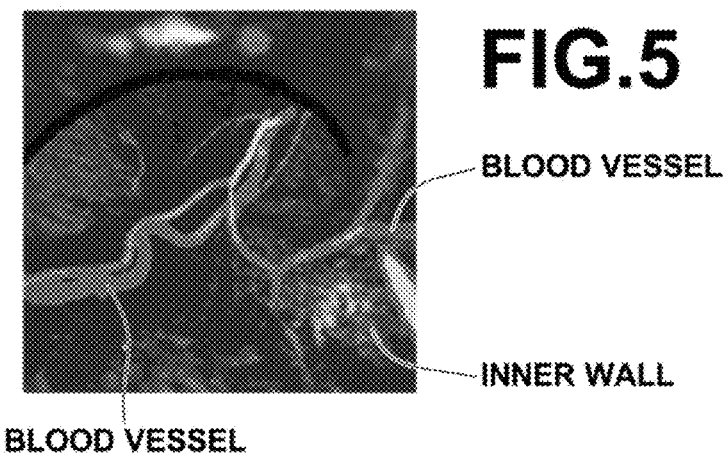

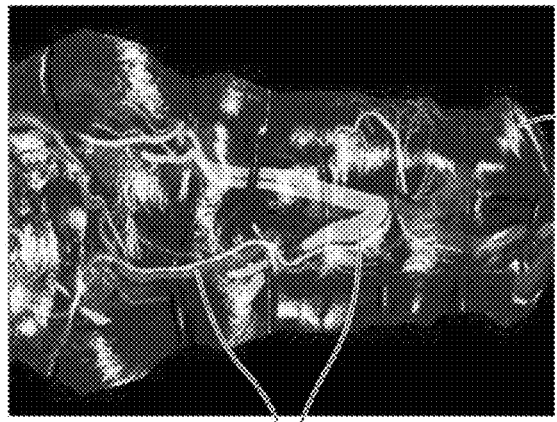
FIG.9
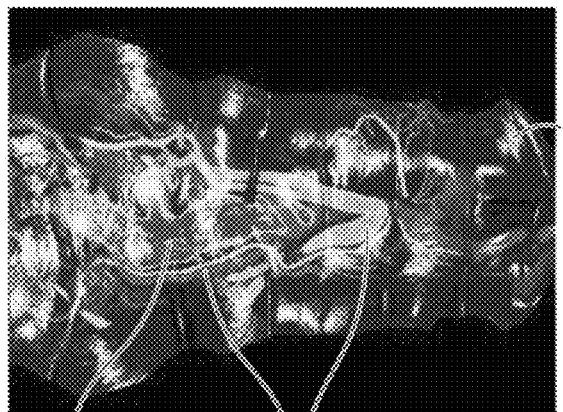
FIG.10
FIG.11
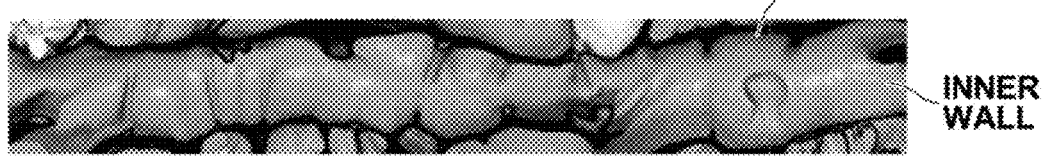

nally intended to observe and the image of the bone, whereby the virtual endoscopic image is difficult to observe the blood vessel or the like.

In view of the circumstances described above, the present disclosure provides a medical image display control apparatus, method, and program capable of displaying a virtual endoscopic image representing the inner wall of a hollow organ and an image that allows for easy observation of, for example, a blood vessel present inside the hollow organ.

A medical image display control apparatus of the present disclosure includes an inner wall image generation unit that generates, based on a three-dimensional image of a subject, an inner wall image representing the inner wall of a hollow organ of the subject, a specific region projection image generation unit that obtains a representative value based on a plurality of voxels on a light ray vector extending outside the hollow organ by a preset distance from each pixel of the inner wall image and generates a specific region projection image by projecting the representative value on the inner wall image, and a display control unit that superimposingly displays the specific region projection image on the inner wall image, in which the specific region projection image generation unit sets some visualization target voxels from the voxels of the three-dimensional image and obtains a representative value of a visualization target voxel in the plurality of voxels on the light ray vector.

The medical image display control apparatus described above may include an organ extraction unit that extracts voxels representing a preset bone or an organ which is not the visualization target, and the specific region projection image generation unit may eliminate the voxels of the preset bone or the organ, and obtains a representative value with voxels of the three-dimensional image after the elimination as the visualization target voxels.

Further, the medical image display control apparatus may include an organ extraction unit that extracts voxels representing a preset organ which is the visualization target, and the specific region projection image generation unit may obtain a representative value with the voxels representing the preset organ as the visualization target voxels.

Still further, the inner wall image generation unit may generate a virtual endoscopic image which is an image of an inner wall of the hollow organ virtually imaged by an endoscope, as the inner wall image.

Further, the inner wall image generation unit may generate an unfolded image which is an image of the hollow organ cut open to unfold the inner wall side, as the inner wall image.

Still further, the inner wall image generation unit may generate an extended cross-sectional image which is an image of the hollow organ longitudinally cut, as the inner wall image.

Further, the specific region projection image generation unit may obtain a maximum value, a minimum value, an average value, or a total value, as the representative value.

Still further, the specific region projection image generation unit may receive selection of one of at least two of the maximum value, minimum value, average value, and total value of the visualization target voxels and may take the received value as the representative value, and the display control unit may display the specific region projection image by allocating a different color according to a magnitude of the representative value.

MEDICAL IMAGE DISPLAY CONTROL APPARATUS, METHOD, AND PROGRAM

CROSS-REFERENCE TO RELATED APPLICATIONS

This application is a Continuation of PCT International Application No. PCT/JP2014/000357 filed on Jan. 24, 2014, which claims priority under 35 U.S.C. § 119 (a) to Japanese Patent Application No. 2013-059673 filed on Mar. 22, 2013. Each of the above applications is hereby expressly incorporated by reference, in its entirety, into the present application.

BACKGROUND

The present disclosure relates to a medical image display control apparatus, method, and program for generating and displaying an inner wall image representing an inner wall of a tubular organ of a subject.

Recently, it has been practiced to extract a hollow organ, such as a large intestine, a small intestine, a bronchus, or a blood vessel, from a three-dimensional image captured by a modality, such as a computed tomography (CT) system, and to use the three-dimensional image of the extracted hollow organ for image diagnosis.

In CT colonography, for example, a technique is proposed in which, based on a three-dimensional image of a large intestine region, a route of an endoscope passing through the large intestine region is determined, then a virtual endoscopic image similar to an image actually taken by an endoscope from a viewpoint while moving the viewpoint along the determined route is generated, and a route to a target point is navigated by displaying the virtual endoscopic image.

A virtual endoscopic image like that described above is an image representing the inner wall of a hollow organ like a large intestine and suited for observing a state of the lumen of a large intestine, but it is not suited for observing, for example, a blood vessel, fat, or a tumor inside the inner wall of the large intestine. Further, the virtual endoscopic image represents a surface state of the inner wall of a hollow organ and is not suited well for detecting a subtly raised polyp in comparison with the surrounding tissues, whereby a lesion may possibly be overlooked.

Hence, Japanese Unexamined Patent Publication No. 11(1999)-076228, Japanese Unexamined Patent Publication No. 2008-054763, and Japanese Unexamined Patent Publication No. 2005-349199 propose to display an organ present outside a hollow organ or the like, in virtual endoscopic image display, by projecting and displaying a maximum value present in a light ray direction of the virtual endoscopic image or an added value on the virtual endoscopic image.

SUMMARY

But, according to the methods described in Japanese Unexamined Patent Publication No. 11(1999)-076228, Japanese Unexamined Patent Publication No. 2008-054763, and Japanese Unexamined Patent Publication No. 2005-349199, if, for example, a bone is present around a large intestine, the bone is also projected on the virtual endoscopic image. This makes it difficult to distinguish between the image of a blood vessel, fat, or a tumor inside the large intestine wall origi- Further, the visualization target organ may be a blood vessel.

Still further, the hollow organ may be a large intestine.

Further, the three-dimensional image may be an image subjected to a digital cleansing process.

A medical image display control method of the present disclosure includes the steps of generating, based on a three-dimensional image of a subject, an inner wall image representing the inner wall of a hollow organ of the subject, obtaining a representative value based on a plurality of voxels on a light ray vector extending outside the hollow organ by a preset distance from each pixel of the inner wall image and generating a specific region projection image by projecting the representative value on the inner wall image, and superimposingly displaying the specific region projection image on the inner wall image, in which when generating the specific region projection image, setting some visualization target voxels from the voxels of the three-dimensional image and obtaining a representative value of a visualization target voxel in the plurality of voxels on the light ray vector.

A medical image display control program of the present disclosure is a program for causing a computer to function as an inner wall image generation unit that generates, based on a three-dimensional image of a subject, an inner wall image representing the inner wall of a hollow organ of the subject, a specific region projection image generation unit that obtains a representative value based on a plurality of voxels on a light ray vector extending outside the hollow organ by a preset distance from each pixel of the inner wall image and generates a specific region projection image by projecting the representative value on the inner wall image, and a display control unit that superimposingly displays the specific region projection image on the inner wall image, in which the specific region projection image generation unit sets some visualization target voxels from the voxels of the three-dimensional image and obtains a representative value of a visualization target voxel in the plurality of voxels on the light ray vector.

According to the medical image display control apparatus, method, and program of the present disclosure, an inner wall image representing an inner wall of a hollow organ of a subject is generated based on a three-dimensional image of the subject, a representative value is obtained based on a plurality of voxels on a light ray vector extending outside the hollow organ by a preset distance from each pixel of the inner wall image and a specific region projection image is generated by projecting the representative value on the inner wall image, and, when the specific region projection image is superimposingly displayed on the inner wall image, some visualization target voxels are set and a representative value of a visualization target voxel in the plurality of voxels on the light ray vector is obtained. Therefore, for example, by excluding voxels of a bone or the like from the voxels of the visualization target, an image of the bone or the like may be excluded from a specific region projection image, whereby a specific region projection image, which allows easy observation of a visualization target blood vessel or the like, may be projected on a virtual endoscopic image and displayed. This may reduce the labor of the observer.

BRIEF DESCRIPTION OF THE DRAWINGS

FIG. 3 is a flowchart for explaining an operation of the medical image diagnosis support system shown in FIG. 1.

FIG. 4 shows an example of a virtual endoscopic image.

FIG. 5 shows an example of a superimposed image in which a specific region projection image is superimposed on a virtual endoscopic image.

FIG. 9 shows an example of a superimposed image in which a specific region projection image is superimposed on an unfolded image.

FIG. 10 shows an example of a superimposed image generated without eliminating voxels of a bone.

FIG. 11 shows an example of an extended cross-sectional image.

DETAILED DESCRIPTION OF THE PREFERRED EMBODIMENTS

Figure 1:
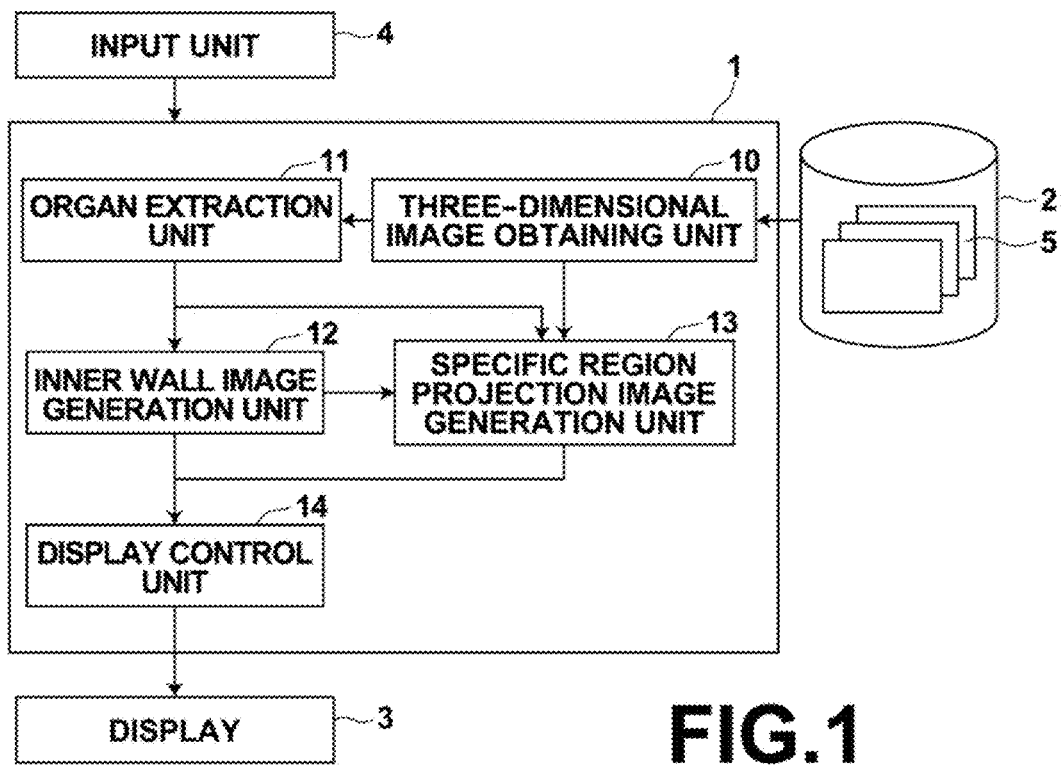
FIG. 1 is a block diagram of a medical image diagnosis support system that uses one embodiment of the medical image display control apparatus, method, and program of the present disclosure, schematically illustrating the configuration thereof.

Hereinafter, a medical image diagnosis support system that uses one embodiment of the medical image display control apparatus, method, and program of the present disclosure will be described in detail with reference to the accompanying drawings. FIG. 1 is a block diagram of the medical image diagnosis support system of the present embodiment.

As illustrated in FIG. 1, the medical image diagnosis support system of the present embodiment includes a medical image display control apparatus 1, a three-dimensional image storage server 2, a display 3, and an input unit 4.

The medical image display control apparatus 1 is a computer on which the medical image display control program of the present embodiment is installed. The medical image display control apparatus 1 includes a central processing unit (CPU) and storage devices, such as a semiconductor memory, a hard disk, a solid state drive (SSD), and the like. The storage device includes the medical image display control program of the present embodiment and execution of the medical image display control program by the central processing unit causes a three-dimensional image obtaining unit 10, an organ extraction unit 11, an inner wall image generation unit 12, a specific region projection image generation unit 13, and a display control unit 14 shown in FIG. 1 to be operated.

The three-dimensional image obtaining unit 10 obtains a three-dimensional image 5 of a subject captured in advance before surgery or examination. The three-dimensional image 5 may be, for example, volume data reconstructed from slice data outputted from a CT system, a magnetic resonance imaging (MRI) system, or the like, volume data outputted from a multi slice (MS) CT system or a cone beam CT system, and other similar volume data. The three-dimensional image 5 is stored in the three-dimensional image storage server 2 in advance with identification information of the subject, and the three-dimensional image obtaining unit 10 reads out a three-dimensional image 5 corresponding to the identification information inputted at the input unit 4 from the three-dimensional image storage server 2. Note that volume data may be generated in the three-dimensional image obtaining unit 10 by obtaining a multitude of slice data.

The three-dimensional image obtaining unit 10 according to the present embodiment is assumed to obtain a three-dimensional image that includes a large intestine. Note that, however, the three-dimensional image obtaining unit 10 is not limited to obtain a three-dimensional image that includes a large intestine and may obtain a three-dimensional image that includes other hollow organs, such as a bronchus, a stomach, or the like.

The organ extraction unit 11 receives the three-dimensional image 5 obtained by the three-dimensional image obtaining unit 10 and extracts voxel data of an organ or a bone of the subject from the received three-dimensional image 5. The organ may be, for example, a large intestine, a small intestine, a liver, a bronchus, or a blood vessel, but not limited to these and other organs may also be extracted, and a decision as to which organ is to be extracted is made by the user using the input unit 4. In the present embodiment, voxel data of a large intestine and a bone are assumed to be extracted and obtained.

A specific method of extracting a large intestine region is as follows. First, a plurality of axial images perpendicular to the body axis is generated based on the three-dimensional image 5 and the outside body area is separated from the inside body area on the basis of the body surface by a known method with respect to each axial image. For example, binarization processing is performed on an inputted axial image, a contour is extracted by contour extraction processing, and the inside of the extracted contour is extracted as the inside (human) body area.

Next, threshold binarization processing is performed on an axial image of inside body area and a large intestine region candidate is extracted in each axial image. More specifically, binarization processing is performed by setting a threshold value corresponding to the CT value of air (e.g., −600 or less), since air is contained in the large intestine tube, and an air region within the body of each axial image is extracted as a large intestine region candidate.

Finally, a large intestine region is obtained by extracting only a portion of the extracted inside body area where large intestine candidates are connected between each of the axial image data. Note that the method of extracting a large intestine region is not limited to that described above, and other known methods, such as Region Growing method, Level Set method, and the like may also be used.

For the method of extracting a bone, any known method may be used, such as the method describe, for example, in R. A. Zoroofi et al., "Segmentation of Pelvis and Femur from Computer Tomography Images", IEICE Technical Report, MI, Medical Image, vol. 100 (No. 596), pp. 99-104, 2001.

The organ extraction unit 11 outputs the extracted voxel data of the large intestine to the inner wall image generation unit 12 and voxel data of a bone to the specific region projection image generation unit 13.

The inner wall image generation unit 12 generates an inner wall image representing the inner wall of the large intestine based on the inputted voxel data of the large intestine. The inner wall image generation unit 12 according to the present embodiment generates, as the inner wall image, a virtual endoscopic image which is an image obtained by virtually imaging the lumen of the large intestine by an endoscope.

More specifically, the inner wall image generation unit 12 generates an image, as the virtual endoscopic image, by central projection method in which voxel data in a plurality of light ray directions extending radially centered on a visual line vector, which bases on a predetermined viewpoint and a visual line direction, are projected on a given projection plane. Specific central projection methods that can be used include, for example, the known volume rendering method and the like.

The viewpoint of the virtual endoscopic image may be set, for example, by specifying an arbitrary point in a three-dimensional image of the large intestine displayed on a display by the user using the input unit 4, or by automatically or manually specifying a given point on the center line of the large intestine extracted based on the voxel data of the large intestine. The visual line direction may also be set by the user by manually setting an arbitrary direction or the travelling direction of the center line of the large intestine may be set as the visual line direction.

The inner wall image generation unit 12 outputs the virtual endoscopic image generated in the manner described above to the display control unit 14.

The specific region projection image generation unit 13 obtains a representative value of voxel data on a light ray vector extending outside the large intestine by a predetermined distance from each pixel of the virtual endoscopic image and generates a specific region projection image by projecting the representative value on the virtual endoscopic image.

Figure 2:
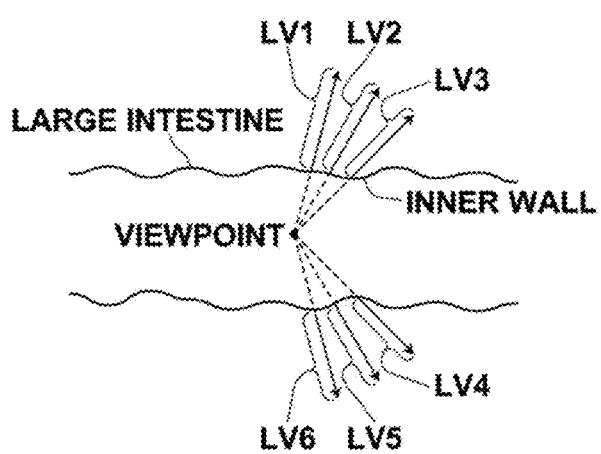
FIG. 2 schematically illustrates an example of light ray vectors extending from each pixel of a virtual endoscopic image.

FIG. 2 schematically illustrates an example of light ray vectors LV1 to LV6 extending from each pixel of a virtual endoscopic image. As illustrated in FIG. 2, the light ray vectors LV1 to LV6 extend in directions which are the same as the light ray directions, with each pixel of the virtual endoscopic image as the origin, and have given distances (lengths). The distances of the light ray vectors LV1 to LV6 are assumed to be preset according to the intended depth of observation. The distances of the light ray vectors LV1 to LV6 may be the same or different.

Further, the distances of the light ray vectors LV1 to LV6 may be changed by the user while observing the display of a specific region projection image, to be described later. The distances may be changed using the input unit 4.

The specific region projection image generation unit 13 obtains, with respect to each of the light ray vectors LV1 to LV6 shown in FIG. 2, a representative value of the voxel data on the vector. The representative value may be a maximum value, a minimum value, an average value, or a total value but, in addition, any value may be used as long as it represents the voxel data on the vector.

Then, each representative value of the voxel data on each of the light ray vectors LV1 to LV6 is projected on the virtual endoscopic image and a specific region projection image is generated.

Here, the specific region projection image generated in the manner described above may include a contrasted blood vessel, fat, a tumor, and the like, but if a bone is present around the large intestine as described above, the image of the bone is also included in the specific region projection image, thereby causing the blood vessel image or the like to be very difficult to observe.

Therefore, the present embodiment generates a specific region projection image by setting visualization target voxels such that an image of a bone or organ which is not the visualization target is not included in the specific region projection image. More specifically, the specific region projection image generation unit 13 of the present embodiment obtains voxel data of a bone outputted from the organ extraction unit 11, eliminates the voxel data of the bone from voxel data of the three-dimensional image 5, and sets the voxel data of the three-dimensional image 5 after the elimination as the visualization target voxels. Then, a representative value of visualization target voxel data in the voxel data on each of the light ray vectors LV1 to LV6 is obtained. This allows the image of the bone which is not the visualization target to be eliminated from the specific region projection image, whereby a specific region projection image that allows, for example, a blood vessel image inside the large intestine wall to be observed easily.

The present embodiment eliminates voxel data of a bone from the visualization target, but not limited to the bone and, for example, voxel data of an organ near the large intestine, such as the kidney, may be eliminated. The elimination target organ is preset by the user using the input unit 4.

The voxel data of a bone, a kidney, or the like may be eliminated by a method in which the voxel data of a bone, a kidney, or the like are set to zero or a method in which the voxel data are masked when a representative value is obtained.

The display control unit 14 receives the virtual endoscopic image generated in the inner wall image generation unit 12 and the specific region projection image generated in the specific region projection image generation unit 13 to generate a superimposed image in which the specific region projection image is superimposed on the virtual endoscopic image, and outputs the superimposed image to the display 3.

The input unit 4 includes a mouse, a keyboard, and the like, and receives an operation input by the user. The input unit 4 according to the present embodiment receives the viewpoint and visual line direction used when generating the virtual endoscopic image, the optical vector length used when generating the specific region projection image, and an input not to set a bone, an organ, or the like as the visualization target, as described above.

An operation of the medical image diagnosis support system of the present embodiment will now be described with reference to a flowchart shown in FIG. 3.

First, identification information of a subject is inputted by the user using the input unit 4, and the three-dimensional image obtaining unit 10 of the medical image display control apparatus 1 reads out and obtains a three-dimensional image 5 corresponding to the inputted identification information of the subject from the three-dimensional image storage server 2 (S10).

The three-dimensional image 5 obtained by the three-dimensional image obtaining unit 10 is inputted to the organ extraction unit 11, and the organ extraction unit 11 extracts and obtains voxel data of the large intestine and a bone based on the inputted three-dimensional image 5 (S12).

The voxel data of the large intestine obtained by the organ extraction unit 11 are inputted to the inner wall image generation unit 12, and the inner wall image generation unit 12 generates a virtual endoscopic image based on the inputted voxel data of the large intestine and outputs the generated virtual endoscopic image to the display control unit 14 (S14). FIG. 4 shows an example of a virtual endoscopic image.

In the meantime, the three-dimensional image 5 obtained by the three-dimensional image obtaining unit 10 and the voxel data of a bone extracted by the organ extraction unit 11 are inputted to the specific region projection image generation unit 13. Then, the specific region projection image generation unit 13 sets visualization target voxel data by eliminating the voxel data of a bone from voxel data of the inputted three-dimensional image (S16), obtains representative values based on the visualization target voxel data and aforementioned light ray vectors LV1 to LV6 to generate a specific region projection image, and outputs the generated specific region projection image to the display control unit 14 (S18).

Figure 6:
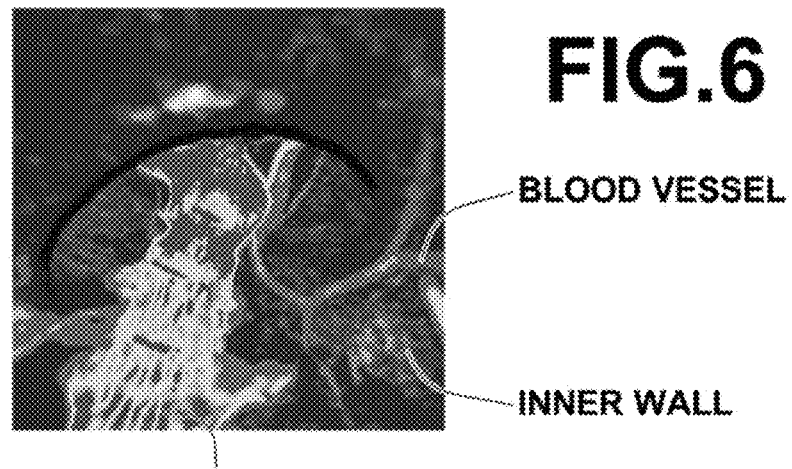
FIG. 6 shows an example of a superimposed image generated without eliminating voxels of a bone.

The display control unit 14 generates a superimposed image by superimposing the specific region projection image on the inputted virtual endoscopic image and displays the generated superimposed image on the display 3 (S20). FIG. 5 shows an example of a superimposed image generated by superimposing a specific region projection image that includes a blood vessel image on a virtual endoscopic image. FIG. 6 is an example of a superimposed image in a case where the specific region projection image is generated without eliminating the voxel data of a bone unlike the present embodiment. As FIG. 6 shows, it is very difficult to observe the blood vessel image because of the appearance of the bone image.

In the medical image diagnosis support system of the foregoing embodiment, the virtual endoscopic image is generated in the inner wall image generation unit 12, but the inner wall image representing the inner wall of a hollow organ is not limited to this and an unfolded image may be generated. The unfolded image is an image of a hollow organ extended linearly and cut open to unfold the inner wall side. The unfolded image is an image obtained by projecting, in each cross-section orthogonal to a length direction of a hollow organ, voxel data of the inner wall on each of light rays extending in all radial directions (360°) from the center line on a two-dimensional image. As the generation method of the unfolded image is well known, for example, by Japanese Unexamined Patent Publication No. 2008-259713 and the like, the detailed description thereof is omitted herein.

Figure 7:
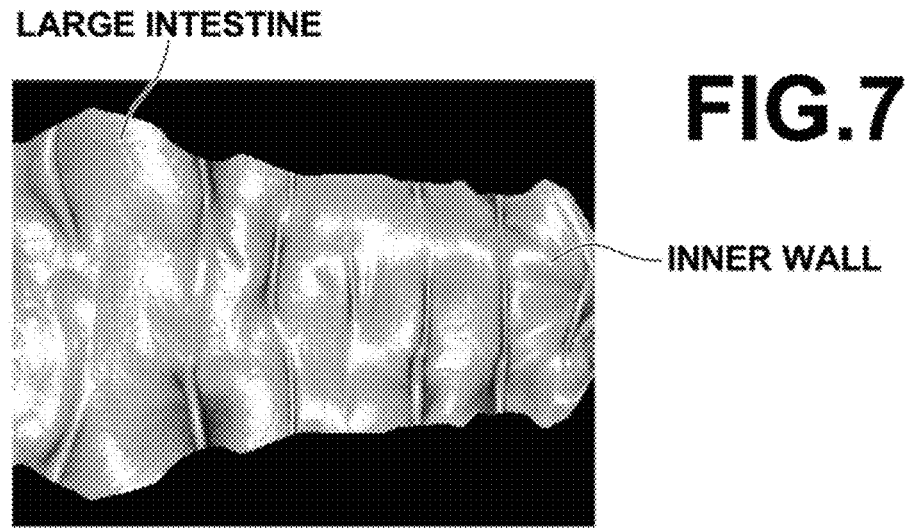
FIG. 7 shows an example of an unfolded image.

FIG. 7 shows an example of an unfolded image of a large intestine. The unfolded image shown in FIG. 7 is an image in which the number of light rays in each cross-section is changed according to the thickness of the large intestine in each cross-section. More specifically, the number of light rays may be set such that the thinner the cross-section, the smaller the number of the light rays, while the thicker the cross-section, the greater the number of the light rays. The change in the number of light rays in each cross-section in the manner described above allows an image close to an actual state of a large intestine being unfolded to be generated, as in the unfolded image shown in FIG. 7. Further, if the number of light rays in each cross-section is unchanged, the unfolded image has a simple rectangular shape. The present embodiment may reduce the observation range in comparison with the foregoing case and hence the efforts of observation may also be reduced.

In a case where the unfolded image is generated in the inner wall image generation unit 12, the specific region projection image generation unit 13 obtains a representative value of voxel data on a light ray vector extending outside the hollow organ by a predetermined distance from each pixel of the unfolded image, and generates a specific region projection image by projecting the representative value on the unfolded image.

Figure 8:
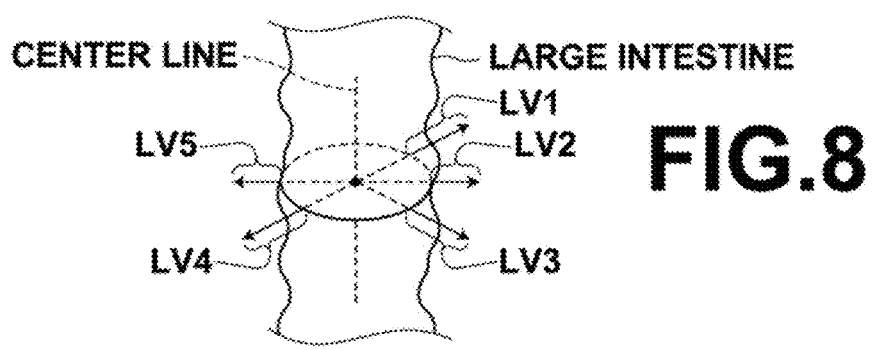
FIG. 8 schematically illustrates an example of light ray vectors extending from each pixel of an unfolded image.

FIG. 8 schematically illustrates an example of light ray vectors LV1 to LV5 extending from each pixel representing the inner wall of an unfolded image. As illustrated in FIG. 8, the light ray vectors LV1 to LV5 are vectors extending in all radial directions from the center line of the large intestine, with each pixel representing the inner wall of the unfolded image as the origin of each vector. The distances (lengths) of the vectors are assumed to be preset according to the intended depth of observation. The distances of the light ray vectors LV1 to LV5 may be the same or different.

The light ray vectors are also set in each cross-section of the large intestine, and the number of light rays may be changed according to the thickness of each cross-section, as in the case of generating the unfolded image. More specifically, the number of light rays may be set such that the thinner the cross-section, the smaller the number of the light rays, while the thicker the cross-section, the greater the number of the light rays.

The representative value of each of the light ray vectors LV1 to LV5 may be a maximum value, a minimum value, an average value, or a total value but, in addition, any value may be used as long as it represents the voxel data on the vector, as in the foregoing embodiment.

Then, a specific region projection image is generated by projecting each representative value of voxel data on each of the light vectors LV1 to LV5. In this case also, the specific region projection image is generated by setting visualization target voxels such that an image of a bone or an organ which is not the visualization target is not included in the specific region projection image, as in the foregoing embodiment. More specifically, voxel data of the bone or kidney are eliminated from the voxel data of the three-dimensional image 5 and voxel data of the three-dimensional image 5 after the elimination are set as the visualization target voxel data, as in the foregoing embodiment. FIG. 9 shows an example of a superimposed image in which a specific region projection image is superimposed on an unfolded image, and FIG. 10 shows an example of a superimposed image generated without eliminating voxels of a bone.

Further, in addition to the unfolded image described above, an extended cross-sectional image may be generated in the inner wall image generation unit 12. The extended cross-sectional image is an image of a hollow organ linearly extended and cut longitudinally. FIG. 11 shows an example of an extended cross-sectional image of a large intestine. As the generation method of the extended cross-sectional image is well known, for example, by Japanese Unexamined Patent Publication No. 2008-259713, Japanese Unexamined Patent Publication No. 2008-259712, Japanese Unexamined Patent Publication No. 2012-024517, and the like, the detailed description thereof is omitted herein.

The generation method of the specific region projection image in a case where the extended cross-sectional image is generated in the inner wall image generation unit 12 is similar to that of the unfolded image other than that the number of directions (angle) in which light ray vectors is set is smaller in the extended cross-sectional image.

In the foregoing embodiment, visualization target voxel data are set by eliminating the voxel data of a bone or the kidney from the voxel data of the three-dimensional image 5. Instead of identifying non-visualization target voxel data, visualization target voxel data may be extracted from voxel data of the three-dimensional image 5 and a specific region projection image may be generated using the extracted voxel data. More specifically, in a case where a blood vessel is taken as the visualization target, the voxel data of the blood vessel may be extracted from the three-dimensional image 5 in the organ extraction unit 11 and a specific region projection image may be generated by obtaining representative values of voxel data of the blood vessel on the light ray vectors.

Note that the visualization target organ is not limited to the blood vessel and the other specific organ may be included. The visualization target organ may be preset by the user using the input unit 4.

In the foregoing embodiment, the description has been made of a case where a large intestine and a blood vessel present inside the wall of the large intestine are displayed, but the observation target hollow organ is not limited to the large intestine and the other hollow organ may also be the observation target, as described above. If the observation target is, for example, a bronchus, a specific region projection image that includes lymph in the bronchus may be generated and displayed. Further, if the observation target is stomach, a specific region projection image that includes a blood vessel or a tumor inside the wall of the stomach may be generated and displayed, as in the large intestine.

Further, when generating the specific region projection image in the foregoing embodiment, a maximum value, a minimum value, an average value, or a total value of the visualization target voxels is obtained as the representative value, and arrangement may be adopted here that any one of these values is selected by the user using the input unit 4. That is, selection of one of at least two of the maximum value, minimum value, average value, and total value is received and the received value is obtained as the representative value.

Then, if the specific region projection image is displayed by the display control unit 14 by allocating a different color to each pixel according to a magnitude of the representative value of each pixel, a superimposed image in which a specific region projection image having a color shade according to the preference of the user is superimposed on an inner wall image may be displayed.

Further, when generating the specific region projection image, an arrangement may be adopted in which one of the visualization target voxels on a light ray vector having a value which is the same as or closest to the representative value is identified, the distance between the voxel and the inner wall (origin of the light ray vector) of the hollow organ is calculated, and the brightness and saturation of the pixel in the specific region projection image are changed according to the distance. For example, if the brightness and saturation are reduced with increase in the distance, the specific region projection image may have a sense of perspective.

In a case where a three-dimensional image that includes a large intestine is obtained and, based on this, an inner wall image and a specific region projection image are generated, as in the foregoing embodiment, a digital cleansing process for eliminating an image of a residue remaining in the large intestine may be performed on the three-dimensional image that includes the large intestine. The digital cleansing process is a process for eliminating an image of a residue portion tagged (labeled) with a contrast agent in advance from the three-dimensional image.

What is claimed is:

1. A medical image display control apparatus, comprising:
   an inner wall image generation unit that generates, based on a three-dimensional image of a subject, an inner wall image representing an inner wall of a hollow organ of the subject;
   a specific region projection image generation unit that obtains a representative value based on a plurality of voxels on a light ray vector extending outside the hollow organ by a preset distance from each pixel of the inner wall image and generates a specific region projection image by projecting the representative value on the inner wall image; and
   a display control unit that superimposingly displays the specific region projection image on the inner wall image,
   wherein the specific region projection image generation unit sets visualization target voxels from the plurality of voxels on the light ray vector and obtains a representative target value thereof, wherein the apparatus further comprising an organ extraction unit that extracts voxels representing an organ which is the visualization target;

wherein the specific region projection image generation unit obtains the representative target value with the voxels representing the organ as the visualization target voxels;

wherein the inner wall image generation unit generates an extended cross-sectional image which is an image of the hollow organ longitudinally cut, as the inner wall image;

wherein the extended cross-sectional image is an image in which voxel data is projected onto a plane, the voxel data presented on a plurality of the light ray vectors extending radially from a center line of the hollow organ; and wherein a number of the plurality of the light ray vectors in each cross-section is changed according to the thickness of the hollow organ in each cross-section, and the number of the light ray vectors being set such that the thinner the cross-section, the smaller the number of light ray vectors, while the thicker the cross-section, the greater the number of light ray vectors.

2. The medical image display control apparatus of claim 1, wherein:
the apparatus comprises an organ extraction unit that extracts voxels representing a bone or an organ which is not the visualization target; and
the specific region projection image generation unit eliminates the voxels of the bone or the organ, and obtains the representative target value with voxels of the three-dimensional image after the elimination as the visualization target voxels.

3. The medical image display control apparatus of claim 1, wherein the inner wall image generation unit generates a virtual endoscopic image which is an image of an inner wall of the hollow organ virtually imaged by an endoscope, as the inner wall image.

4. The medical image display control apparatus of claim 1, wherein the inner wall image generation unit generates an unfolded image which is an image of the hollow organ cut open to unfold the inner wall side, as the inner wall image.

5. The medical image display control apparatus of claim 1, the specific region projection image generation unit obtains a maximum value, a minimum value, an average value, or a total value, as the representative value.

6. The medical image display control apparatus of claim 1, wherein:
the specific region projection image generation unit receives selection of one of at least two of the maximum value, minimum value, average value, and total value of the visualization target voxels and takes the received value as the representative value; and
the display control unit displays the specific region projection image by allocating a different color according to a magnitude of the representative value.

7. The medical image display control apparatus of claim 1, wherein the visualization target organ is a blood vessel.

8. The medical image display control apparatus of claim 1, wherein the hollow organ is a large intestine.

9. The medical image display control apparatus of claim 8, wherein the three-dimensional image is an image subjected to a digital cleansing process.

10. A medical image display method, comprising the steps of:
generating, based on a three-dimensional image of a subject, an inner wall image representing the inner wall of a hollow organ of the subject;
obtaining a representative value based on a plurality of voxels on a light ray vector extending outside the hollow organ by a preset distance from each pixel of the inner wall image and generating a specific region projection image by projecting the representative value on the inner wall image; and
superimposingly displaying the specific region projection image on the inner wall image,
wherein, when generating the specific region projection image, setting visualization target voxels from the plurality of voxels on the light ray vector and obtaining a representative target value thereof,
wherein the apparatus further comprising an organ extraction unit that extracts voxels representing an organ which is the visualization target;
wherein the specific region projection image generation unit obtains the representative target value with the voxels representing the organ as the visualization target voxels;
wherein the inner wall image generation unit generates an extended cross-sectional image which is an image of the hollow organ longitudinally cut, as the inner wall image;
wherein the extended cross-sectional image is an image in which voxel data is projected onto a plane, the voxel data presented on a plurality of the light ray vectors extending radially from a center line of the hollow organ; and
wherein a number of the plurality of the light ray vectors in each cross-section is changed according to the thickness of the hollow organ in each cross-section, and the number of the light ray vectors being set such that the thinner the cross-section, the smaller the number of light ray vectors, while the thicker the cross-section, the greater the number of light ray vectors.

11. A non-transitory computer-readable recording medium containing a medical image display control program for causing a computer to function as:
an inner wall image generation unit that generates, based on a three-dimensional image of a subject, an inner wall image representing the inner wall of a hollow organ of the subject;
a specific region projection image generation unit that obtains a representative value based on a plurality of voxels on a light ray vector extending outside the hollow organ by a preset distance from each pixel of the inner wall image and generates a specific region projection image by projecting the representative value on the inner wall image; and
a display control unit that superimposingly displays the specific region projection image on the inner wall image,
wherein the specific region projection image generation unit sets visualization target voxels from the plurality of voxels of the light ray vector and obtains a representative target value thereof,
wherein the apparatus further comprising an organ extraction unit that extracts voxels representing an organ which is the visualization target; and
wherein the specific region projection image generation unit obtains the representative target value with the voxels representing the organ as the visualization target voxels;

wherein the inner wall image generation unit generates an extended cross-sectional image which is an image of the hollow organ longitudinally cut, as the inner wall image;

wherein the extended cross-sectional image is an image in which voxel data is projected onto a plane, the voxel data presented on a plurality of the light ray vectors extending radially from a center line of the hollow organ; and wherein a number of the plurality of the light ray vectors in each cross-section is changed according to the thickness of the hollow organ in each cross-section, and the number of the light ray vectors being set such that the thinner the cross-section, the smaller the number of light ray vectors, while the thicker the cross-section, the greater the number of light ray vectors.

* * * * *